United States Patent [19]

Mabelis

[11] Patent Number: 4,578,483

[45] Date of Patent: Mar. 25, 1986

[54] GIBBERELLIN AMINE SALTS

[75] Inventor: Richard P. Mabelis, Cheshire, England

[73] Assignee: Imperial Chemical Industries Plc, London, England

[21] Appl. No.: 549,444

[22] Filed: Nov. 7, 1983

[30] Foreign Application Priority Data

Dec. 1, 1982 [GB] United Kingdom ............... 8234274

[51] Int. Cl.$^4$ ............................................ C07D 307/00
[52] U.S. Cl. .................................. 549/297; 546/269; 549/60; 435/65
[58] Field of Search ................... 549/297, 60; 546/269

[56] References Cited

U.S. PATENT DOCUMENTS 4,156,684 5/1979 Crutcher ............................. 549/297

FOREIGN PATENT DOCUMENTS 1174924 12/1969 United Kingdom .
1538502 1/1979 United Kingdom .

OTHER PUBLICATIONS

Chemical Abstracts vol. 85, No. 1, Jul. 5, 1976, p. 476, Abrstract 5900h.

Primary Examiner—Jane T. Fan
Attorney, Agent, or Firm—Cushman, Darby & Cushman

[57] ABSTRACT

The salt of $GA_4$ and/or $GA_7$ with an amine of formula $R^1CH_2NHR^2$ wherein $R^1$ is optionally substituted phenyl, thienyl or pyridyl and $R^2$ is alkyl or alkynyl. The salts are useful in the preparation of $GA_4/GA_7$ and their separation from $GA_3$.

4 Claims, No Drawings

GIBBERELLIN AMINE SALTS

This invention relates to new plant growth regulators and more particularly it relates to new salts of gibberellins which are useful in separating specific gibberellins from fermentation broths containing mixtures of gibberellins.

The gibberellins are a class of plant-growth hormones which occur naturally in various higher plants and in some micro-organisms. More than fifty naturally-occurring gibberellins are known, and more synthetic compounds have been prepared. Although chemically closely related, the gibberellins differ quantitatively and qualitatively from each other in their effects on some higher plants. Only three gibberellins have found extensive commercial use. These are gibberellic acid (gibberellin $A_3$, $GA_3$), gibberellin $A_4$ ($GA_4$) and gibberellin $A_7$ ($GA_7$), all of which are manufactured by fermentation of the fungus *Gibberella fujikuroi* (also known as *Fusarium moiliforme*). The chemical structures of these three gibberellins are as follows:

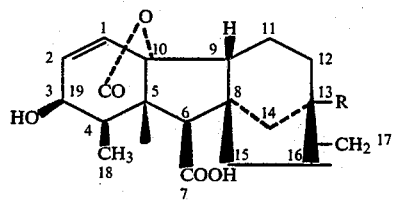

| | | |
|---|---|---|
| $GA_3$ | R = hydroxy, | 1,2-double bond present |
| $GA_4$ | R = H, | 1,2-double bond absent |
| $GA_7$ | R = H, | 1,2-double bond present |

The fermentation of *Gibberella fujikuoroi* normally results in the production of a mixture of gibberellins amongst which $GA_3$, $GA_4$ and $GA_7$ predominate, $GA_3$ being the most abundant. Other gibberellins, however, especially gibberellins $A_{13}$, are also present in lesser amounts. These products are normally extracted from the fermentation broth with a water-immiscible solvent, such as ethyl acetate, ethyl methyl ketone or n-butanol, although other isolation procedures have been described. $GA_4$ and $GA_7$, which differ structurally one from the other only by the absence or presence of an olefinic double bond, are very difficult to separate one from the other and the commercial material normally contains a mixture of the two compounds. $GA_3$, however, contains an additional hydroxy group and it is possible to separate $GA_3$ from $GA_4/GA_7$. It is commercially desirable to separate $GA_3$, and $GA_4$ mixed with $GA_7$, from a mixture containing all three components because the plant-growth-regulatory effects of $GA_3$, and $GA_4/GA_7$ differ in some important respects, and the compounds have therefore distinct and specific practical applications. For example, in some plant species the mixture $GA_4/GA_7$ promotes fruit set without causing the excessive vegetative growth which would be produced by $GA_3$. Another difference is that $GA_4/GA_7$ is effective in breaking the dormancy of some seeds in a situation where $GA_3$ would produce excessive and undesirable hypocotyl extension.

In United Kingdom Specification No. 1,174,924 there is described a method for separating $GA_3$, and a mixture of $GA_4$ and $GA_7$, from a culture filtrate of *Giberella fujikuroi* containing all three compounds, which method is based on the different partition coefficients of $GA_3$ and $GA_4/GA_7$ between certain organic solvents and water within a particular pH range. If therefore it is desired to produce $GA_4/GA_7$, the culture filtrate is extracted with an organic water-immiscible solvent at a pH of between 4 and 8.5. This produces an organic extract rich in $GA_4/GA_7$, leaving an aqueous broth rich in $GA_3$. Even after selective enrichment of the organic extract in $GA_4/GA_7$ by this means, however, it is frequently very difficult to precipitate these gibberellins from the extract, probably because even at this pH a number of substances other than $GA_4/GA_7$ is extracted from the culture filtrate, and the presence of these other substances, especially gibberellin $A_{13}$, inhibits precipitation of $GA_4/GA_7$.

In United Kingdom Specification No. 1,538,502 there are described certain salts of gibberellins with amines. These salts include salts of $GA_4$ and $GA_7$ with certain amines, and they are prepared by reacting the isolated gibberellin with the amine. The salts are used to prepare compositions which may be used at a lower rate of application than the gibberellins themselves. No salt of a gibberellin with an aryl-alkylamine is however described in said specification.

We have now found, and herein lies our invention, that addition of an N-hydrocarbyl-N-arylmethyl amine to an organic extract of a suitable fermentation broth selectively precipitates the salts of $GA_4$ and $GA_7$ with said amine, leaving $GA_3$ substantially in solution. The advantage of the invention is firstly to improve, in respect of yield and of convenience, the isolation of $GA_4/GA_7$, and secondly to improve the separation of $GA_4/GA_7$ from $GA_3$.

According to the invention there is provided a salt of gibberellin $A_4$ ($GA_4$) or of gibberellin $A_7$ ($GA_7$) or of a mixture of gibberellins $A_4$ and $A_7$, with an amine of the formula $R^1CH_2NHR^2$, wherein $R^1$ is a phenyl, thienyl or pyridyl radical which may be unsubstituted or which may bear one or more substituents selected from chlorine atoms, and alkyl substituents of up to 4 carbon atoms, for example methyl and ethyl substituents, and wherein $R^2$ is a straight-chain alkyl or alkynyl radical of up to 3 carbon atoms, for example the methyl, ethyl or propargyl radical.

$R^1$ is preferably phenyl, 3-chlorophenyl or 3-pyridyl, and $R^2$ is preferably methyl, ethyl or propargyl.

Specific amines which may be used to form a salt of the invention are N-benzyl-N-methylamine, N-benzyl-N-ethylamine, N-3-chlorobenzyl-N-methylamine, N-4-chlorobenzyl-N-methylamine, N-benzyl-N-propargylamine, N-methyl-N-(3-pyridylmethyl) amine, N-methyl-N-(2-pyridylmethyl) amine and N-methyl-N-(6-methyl-pyrid-2-ylmethyl) amine, and of these a particularly preferred amine is N-benzyl-N-methylamine.

The salt of the gibberellin and the amine is usually prepared from an alcoholic solution and under these conditions the salt precipitates as an alcohol solvate thereof.

According to a further feature of the invention there is provided a process for the manufacture of a salt of $GA_4$ or $GA_7$, or a mixture thereof, with an amine of the formula $R^1CH_2NHR^2$, wherein $R^1$ and $R^2$ have the meanings stated above, which comprises mixing an amine of the above formula with an organic extract of a culture filtrate of *Gibberella fujikuroi* and recovering the precipitated salt from the mixture.

The organic extract is preferably an ethyl acetate extract, and this extract is preferably concentrated and then diluted, before mixing with the amine, with an aliphatic alcohol of 3 to 5 carbon atoms, for example isopropanol, n-propanol, n-butanol, s-butanol, isobutanol, t-amyl alcohol, 3-methyl-1-butanol or tetrahydrofurfuryl alcohol. The mixing of the amine and extract, and the recovering of the precipitated salt, may be carried out at any temperature between −80° C. and +170° C., but is preferably carried out at plant temperature.

The recovery of the precipitated salt is preferably carried out by filtration, but centrifugation may equally well be used.

According to a further feature of the invention there is provided a process for the isolation of a mixture of $GA_4$ and $GA_7$ from a fermentation broth containing these compounds, which comprises extracting the culture filtrate from the fermentation with an organic solvent, precipitating from said extract by the process described above a salt of $GA_4/GA_7$ with an amine of the formula $R^1CH_2NHR^2$, wherein $R^1$ and $R^2$ have the meanings stated above, and isolating the $GA_4/GA_7$ from said salt by thereof reaction with an acid.

A suitable acid is, for example, citric acid, especially as its hydrate, or oxalic, acetic, hydrochloric or toluene-p-sulphonic acid. The reaction of the amine salt with an acid is preferably carried out in an aqueous medium, for example in a mixture of methanol and water, and the mixture of $GA^4$ and $GA_7$ is preferably isolated from the reaction mixture by filtration.

The process of the invention for the isolation of a mixture of $GA_4$ and $GA_7$ has advantages over the prior art isolation procedures as follows:

(a) The mixture of $GA_4/GA_7$ obtained by the process of the invention is sufficiently pure that it may be used directly after isolation from the acidification step, and no recrystallisation is necessary.

(b) The yield of the mixture $GA_4/GA_7$ from the process of the invention is higher than that obtained by a process not involving the salt-formation step. Indeed, further $GA_4/GA_7$ may be obtained from discarded liquors from such an isolation process by using the salt formation of the invention.

(c) The mixture $GA_4/GA_7$ obtained by the process of the invention is purer, especially in its freedom from $GA_3$ and other gibberellins, than that obtained by prior art processes.

The invention is illustrated but not limited by the following Examples:

EXAMPLE 1

Sodium chloride (13 900 kg) was added to the filtrate (69,500 liters) obtained by filtration of the whole broth (68,000 liters) of fermentation of *Gibberella fujikuroi* and the mixture was extracted with ethyl acetate (23,000 liters) in a centrifugal extractor at a pH of between 4.2 and 4.4. The extract was concentrated to 360 liters and assayed by gas-liquid and high-performance liquid chromatography for gibberellins. It was found to contain 60.3 kg of total gibberellins as follows (% by weight):

|  | % |
|---|---|
| $GA_3$ | 19.9 |
| $GA_4$ | 11.3 |
| $GA_7$ | 63.5 |
| Other gibberellins (mostly $GA_9$ and $GA_{13}$) | 5.3 |
|  | 100.0 | n-Propanol (720 liters) was added, the mixture was stirred at between 15° and 20° C. and N-benzyl-N-methylamine (77 kg) was added. The mixture was stirred for 2 hours and then filtered, and the solid residue was washed three times with n-propanol (50 liters each time) and then dried at 60° C. There was thus obtained an N-benzyl-N-methylamine salt of mixed gibberellins as a mono-n-propanol solvate (63.3 kg) which was shown by gas-liquid chromatographic assay to contain gibberellins (as their salt—solvates) in the following proportions:

|  | % |
|---|---|
| $GA_3$ | 7.3 |
| $GA_4$ | 12.1 |
| $GA_7$ | 79.7 |
| Others | 0.9 |
|  | 100.0 |

EXAMPLE 2

A solution of the N-benzyl-N-methylamine salt (131.6 kg obtained from two batches of gibberellins as described in Example 1), in a mixture of methanol (240 liters) and water (120 liters) was passed at 20° C. through a 30 micron line-filter, and the line was washed with a 2:1 v/v mixture of methanol and water (54 liters). A solution of citric acid hydrate (68 kg) in water (120 liters) was added, via a 30 micron line-filter, to the stirred mixture of filtrate and washing, and the line was washed with water (44 liters). The whole mixture was stirred at 20° C. and water (40 liters) was added, whereupon crystallisation began. The stirred mixture was cooled to 12° C., further water (200 liters) was added, and the mixture was stirred for 1 hour and then filtered.

The solid product was washed three times with water (70 liters each time) and then dried at 60° C. There was thus obtained a mixture of the hydrates of gibberellins $A_4$ and $A_7$ (65.7 kg) which was shown by gas-liquid chromatographic assay and Karl Fischer assay for water to be made up as follows:

|  | % |
|---|---|
| $GA_4$ | 14.7 |
| $GA_7$ | 77.6 |
| other Gibberellins (mostly $GA_9$ and $GA_3$) | 2.2 |
| Water | 5.5 |
|  | 100.0 |

EXAMPLE 3

Isopropanol (15 m) was added to a concentrated ethyl acetate extract (5 ml) of a culture filtrate obtained as described in Example 1, the mixture was stirred at laboratory temperature and N-benzyl-N-methylamine (1.7 ml) was added. The mixture was cooled to 5° C. and filtered, and the solid residue was washed twice with isopropanol (2 ml each time), and then dried at laboratory temperature. There was thus obtained an N-benzyl-N-methylamine salt of mixed gibberellins (predominantly $GA_4$ and $GA_7$) as the isopropanol solvate, yield 0.91 g. Assay showed that $GA_4/GA_7$ comprised 54.0% by weight of the total salt solvate.

The process described above was repeated using different alcohols, and there were thus obtained N-benzyl-N-methylamine salts as shown in the following table:

| Alcohol | Volume of Alcohol (ml) | Yield of Salt (g) | % $GA_4/GA_7$ of total solid |
|---|---|---|---|
| n-butanol | 5 | 1.11 | 54.6 |
| s-butanol | 15 | 1.17 | 45.8 |
| isobutanol | 15 | 1.39 | 43.1 |
| t-amyl alcohol | 15 | 0.82 | 50.8 |
| 3-methyl-1-butanol | 5 | 1.22 | 49.1 |
| tetrahydrofurfuryl alcohol | 10 | 0.97 | 46.3 |

EXAMPLE 4

The process described in Example 3 was repeated using various amounts of extract and of various alcohols, and using different temperatures for the salt formation step. There were thus obtained N-benzyl-N-methylamine salts as shown in the following table:

| Volume of extract (ml) | Alcohol and volume (ml) | Temperature (°C.) | Yield of Salt (g) | $GA_4/GA_7$ of total solid |
|---|---|---|---|---|
| 10 | n-propanol (20) | −78 | 2.9 | 45.1 |
| 15 | isopropanol (30) | 43 | 2.7 | 60.7 |
| 15 | isopropanol (30) | 63 | 3.2 | 56.3 |
| 10 | 3-methyl-1-butanol (10) | 93 | 2.6 | 50.1 |
| 15 | 3-methyl-1-butanol (30) | 125* | 4.1 | 49.9 |
| 15 | tetrahydro-furfuryl alcohol (30) | 170* | 2.4 | 51.6 |

*The ethyl acetate was completely removed by evaporation and the alcohol was the sole solvent used for the salt formation step.

EXAMPLE 5

The process described in Example 3 was repeated using 10 ml of concentrated ethyl acetate extract and various amines in place of N-benzyl-N-methylamine. There were thus obtained salts as shown in the following table:

| Amine | Alcohol and volume (ml) | Temperature (°C.) | Yield of salt (g) | % $GA_4/GA_7$ of total solid |
|---|---|---|---|---|
| N—benzyl-N—ethylamine | isopropanol (10) | 4 | 2.42 | 45.7 |
| N—benzyl-N—propargylamine | isopropanol (25) | 5 | 3.24 | 46.7 |
| N—3-chlorobenzyl-N—methylamine | isobutanol (30) | −20 | 3.34 | 42.0 |
| N—4-chlorobenzyl-N—methylamine | isobutanol (30) | −20 | 1.06 | 39.4 |
| N—methyl-N—(pyrid-3-ylmethyl)-amine | isopropanol (10) | 4 | 1.41 | 50.7 |
| N—methyl-N—(pyrid-2-ylmethyl)-amine | n-propanol (20) | 0 | 1.37 | 32.3 |
| N—methyl-N—(6-methylpyrid-2-ylmethyl) amine | isobutanol (30) | −20 | 3.38 | 43.4 |

EXAMPLE 6

A suspension of oxalic acid (5.6 g) in water (20 ml) was added to a solution of the N-benzyl-N-methylamine salt of mixed gibberellins mono-n-propanol solvate (Example 1; 20 g) in a mixture of water (20 ml) and methanol (40 ml). Water (40 ml) was added and the mixture was stirred at 22° C. for 30 minutes and then filtered The solid product was washed twice with water (12 ml each time) and dried at 50° C., and there was thus obtained a mixture of the hydrates of gibberellins $A_4$ and $A_7$ (11.8 g) shown by gas-liquid chromatography to contain 82.4% by weight of gibberellin $A_7$ and 14.6% by weight of gibberellin $A_4$.

The process described above was repeated using the appropriate acid in place of oxalic acid, and the appropriate amounts of solvent water. There were thus obtained the yields of $GA_4/GA_7$ shown in the following table:

| Acid | Amount of Acid used | Amount of water used dissolve acid (ml) | Amount of water used to precipitate product (ml) | Yield of $GA_4/GA_7$ (g) |
|---|---|---|---|---|
| glacial acetic acid | 10 ml | — | 80 | 9.14 |
| concentrated aqueous hydrochloric acid | 6 ml | — | 60 | 10.01 |
| toluene-p-sulphonic acid | 10 g | 0 | 50 | 8.64 |

In all cases assay showed the product to contain more than 95% by weight of the hydrates of $GA_4$ and $GA_7$.

I claim:

1. A mixture of salts of gibberellin $A_4$ ($GA_4$) and of gibberellin $A_7$ ($GA_7$) with an amine of the formula $R^1CH_2NHR^2$, wherein $R^1$ is a phenyl, thienyl or pyridyl radical unsubstituted or substituted with chlorine or $C_1$-$C_4$ alkyl, and $R^2$ is a straight chain alkyl or alkynyl radical of up to 3 carbon atoms.

2. A salt as claimed in claim 1 wherein $R^1$ is phenyl, 3-chlorophenyl or 3-pyridyl.

3. A salt as claimed in either of claims 1 or 2 wherein $R^2$ is methyl, ethyl or propargyl.

4. A salt as claimed in any of claims 1 to 3 in which the amine is N-benzyl-N-methyl amine.

* * * * *